United States Patent [19]

Barberet et al.

[11] Patent Number: Plant 5,788

[45] Date of Patent: Aug. 26, 1986

[54] CARNATION NAMED LONDRINO

[75] Inventors: Nicole Barberet; Yves Ducloux, both of Antibes, France

[73] Assignee: Laboratoire de Physiologie Vegetale de la Londe, La Londe, France

[21] Appl. No.: 613,714

[22] Filed: May 24, 1984

[51] Int. Cl.[4] ..... A01H 5/00

[52] U.S. Cl. ..... Plt./71

[58] Field of Search ..... Plt./71

*Primary Examiner*—James R. Feyrer

*Attorney, Agent, or Firm*—Charles W. Rummler; John B. Lungmus

[57] ABSTRACT

A new variety of spray carnation distinguished by its small, dark pink blooms which are produced profusely with a recurrent year around blooming habit on a tall plant having a strong, vigorous and upright growth habit with above average quantity of foliage, the flower petals being of monochrome coloration with the exception of a lightening of the color at the very edges of the petals.

1 Drawing Figure

BACKGROUND OF THE INVENTION

This spray carnation cultivar was developed by us during the course of breeding efforts carried on at La Londe, Les Maures, Var., France, since about 1977, with the object of producing a new variety in the pink color range producing flowers of good quality and attractive coloration suitable for large scale greenhouse culture. The new plant originated as a seedling resulting from our crossing of selected varieties from breeding stock maintained by us at our laboratories at La Londe and this seedling was selected for propagation and test because of the very nice shape and coloration of its blooms. Original propagation of this new seedling, by means of cuttings from the parent plant, was done at our La Londe laboratory and then carried on through several successive generations which demonstrated that the novel characteristics of the new plant hold true from generation to generation and appear to be firmly fixed.

DESCRIPTION OF THE DRAWING

Our new variety of spray carnation is illustrated by the accompanying photographic drawing, which shows a typical stem of this variety in full color showing buds in various stages of opening and a fully developed bloom, the colors shown being as nearly true as it is possible to reasonably obtain by conventional photographic procedures.

DESCRIPTION OF THE NEW PLANT

The following is a detailed description of our new carnation cultivar based upon observations of plants grown at La Londe in the late Fall of 1983, the color designations being according to The R.H.S. Colour Chart published by The Royal Horticultural Society of London, England.

THE PLANT

Origin: Seedling.

Parentage:

*Seed parent.*—Stock Variety No. 73 MV 7 (unpatented);

*Pollen parent.*—Stock Variety No. 72 MR 3 (unpatented); these unnamed varieties being individually identified in our permanent records and maintained for breeding purposes in our carnation collection at La Londe.

Classification:

*Botanic.*—*Dianthus caryophyllus L.*

*Commercial.*—Spray carnation.

Form: Bush of erect shape with at least four stems emitted near the ground.

Height: About 96 cm. in average.

Growth: Vigorous, upright and rather rigid in strength.

Branching character: The spray is racemose, each stem bearing 4 or 5 secondary branches (pedicels) which may bear one or more supplementary branches.

Foliage:

*Quantity.*—Medium with at least 120 leaves.

*Leaf size.*—About 11 cm. long and about 1.2 cm. wide.

*Leaf shape.*—Amplexicaul and elongate with acuminate apex, taken at the seventh node and having a margin that is sometimes very slightly curved.

*Texture.*—Leathery.

*Ribs, veins and rachis.*—Hardly noticeable.

*Color.*—Upper side — 189A-B. Under side — 189A-B.

THE BUD

Shape: Somewhat cylindrical.

Size: Medium.

*Diameter.*—About 1.1 cm. in average.

*Length.*—About 2.6 cm. in average.

Color of petals:

*When sepals first divide.*—68B with 68C at the petal edges.

*When petals begin to unfurl.*—68B with 68C at the edge.

Sepals:

Number.—Mostly five and hooded over the bud.

*Shape.*—Joined at the lower part and sharply pointed at the apex.

*Character.*—The sepals stand up when the flowers open.

*Color.*—Outside — 138B and 145B with longitudinal striae.

Calyx:

*Shape.*—Long.

*Aspect.*—Smooth.

*Splitting.*—The calyx does not split.

THE FLOWER

Blooming habit: Recurrent, blooming profusely the year around with a tendency to give fewer blooms in the Fall.

Size of bloom: Small, averaging about 5 cm. in diameter and about 4.5 cm. in depth.

Borne: In clusters.

Shape:

*When bloom first opens.*—High centered.

*When bloom matures.*—Dome-shaped.

Petalage:

*Number of petals.*—'About 34 in average.

*Arrangement.*—Imbricated.

*Form.*—Fan-shaped with rounded edges and serrated at the apex margin.

*Texture.*—Soft.

*Appearance.*—Satiny.

*Color.*—Outer Petals: Body — 65A and 65B at the edge. Base — Greenish yellow. Reverse side — 65A and 65C at the edge. Inside Petals: Body — 65A and 65C at the edge. Base — Greenish yellow. Reverse side — 65A and 65C at the edge.

Fragrance: Rather strong.

Persistence: The petals hang on and dry.

Lasting quality:

*As a cut flower for vase keeping.*—At least ten days.

REPRODUCTIVE ORGANS

Stamens:

*Number.*—14 to 23 arranged around the ovary.

*Anthers.*—About 4 mm. long. Color: Whitish.

*Filaments.*—Color: Whitish.

Pistils: Usually two in number.

Styles:

*Color.*—Whitish.

Stigmas:

*Color.*—Whitish.

Character of ovaries: Small and ribbed.

We claim:

1. The new and distinct variety of spray carnation, substantially as herein shown and described, characterized in particular by its small, well shaped flowers of dark pink coloration.

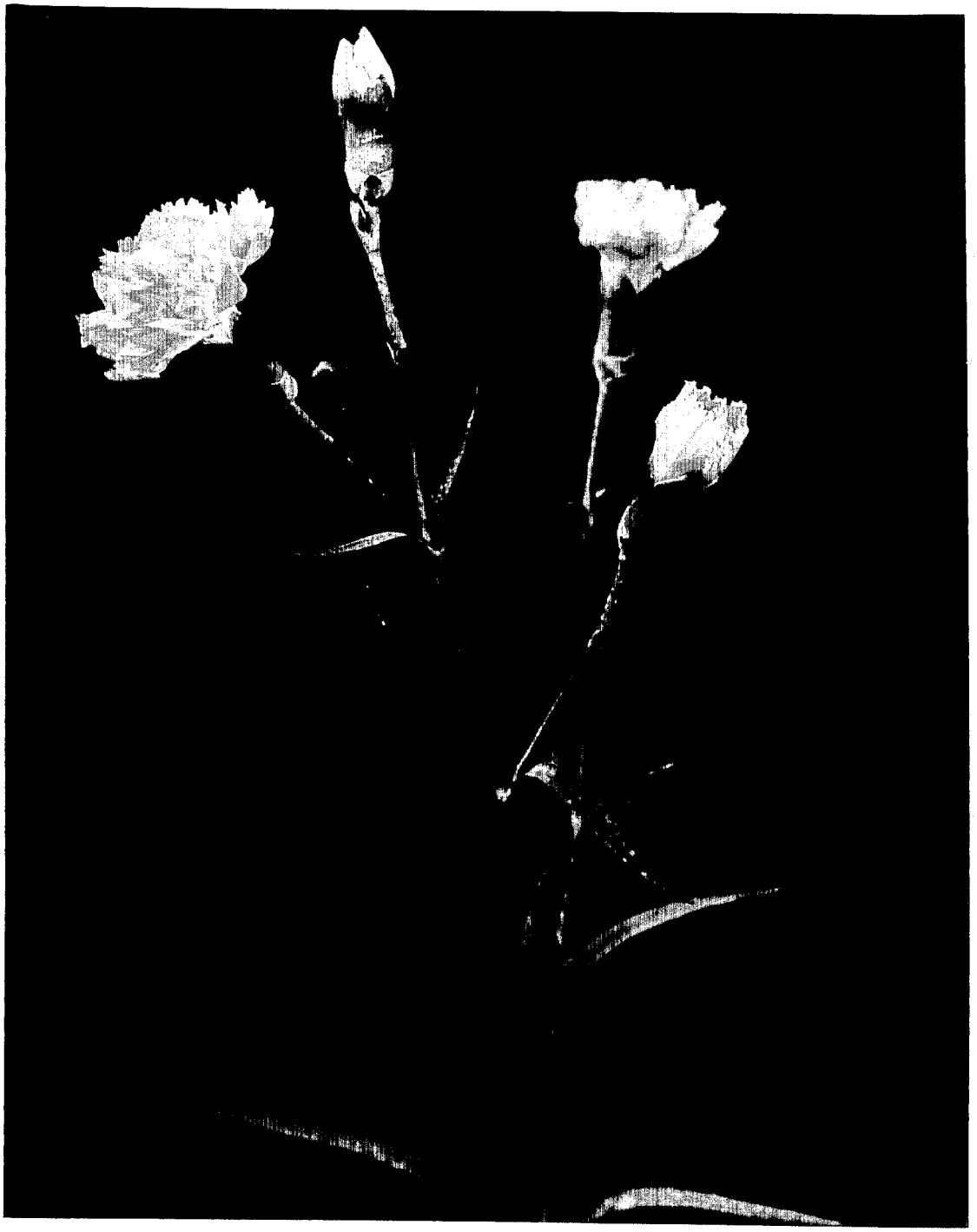

* * * * *